United States Patent
Tsimerman et al.

(10) Patent No.: US 7,021,798 B2
(45) Date of Patent: Apr. 4, 2006

(54) DENTAL MIRROR

(76) Inventors: Efraim Tsimerman, Suite 903 West, 480 Queens Quay West, Toronto, Ontario (CA), M5V 2Y5; Emil Chouster, Apt. 410, 360 Ridelle Avenue, Toronto, Ontario (CA)

( * ) Notice: Subject to any disclaimer, the term of this patent is extended or adjusted under 35 U.S.C. 154(b) by 261 days.

(21) Appl. No.: 10/274,157

(22) Filed: Oct. 21, 2002

(65) Prior Publication Data

US 2004/0076019 A1 Apr. 22, 2004

(51) Int. Cl.
*B60Q 3/04* (2006.01)

(52) U.S. Cl. .................. 362/362; 362/368; 362/418; 362/430; 362/800

(58) Field of Classification Search ............ 362/362, 362/368, 418, 430, 800
See application file for complete search history.

(56) References Cited

U.S. PATENT DOCUMENTS

| | | | |
|---|---|---|---|
| 3,031,930 A | 5/1962 | Kafig | |
| 3,755,903 A | 9/1973 | Spinello | |
| 3,826,005 A | 7/1974 | Spinello | |
| 3,849,889 A | 11/1974 | Rosander | |
| 3,859,987 A | 1/1975 | Holstad | |
| 3,969,824 A | 7/1976 | Widen et al. | |
| 3,986,266 A | 10/1976 | Vellender | |
| 4,261,637 A * | 4/1981 | King ...................... | 359/508 |
| 4,408,991 A * | 10/1983 | Engel ...................... | 433/30 |
| 5,139,420 A | 8/1992 | Walker | |
| 5,295,826 A | 3/1994 | Yandell et al. | |
| 5,654,824 A | 8/1997 | Tarr et al. | |
| 6,247,924 B1 | 6/2001 | Gunnarsson | |
| 6,575,744 B1 * | 6/2003 | Oshida ...................... | 433/31 |
| 2002/0058230 A1 | 5/2002 | Savin et al. | |

FOREIGN PATENT DOCUMENTS

| | | |
|---|---|---|
| EP | 0 950 371 A1 | 11/1997 |
| JP | 10315713 | 11/1998 |
| JP | 11297264 | 10/1999 |
| JP | 2000212436 | 7/2000 |
| WO | WO 01/97681 A3 | 12/2001 |

OTHER PUBLICATIONS

Patent Abstracts of Japan 2000325308.

* cited by examiner

*Primary Examiner*—Stephen Husar
*Assistant Examiner*—Bertrand Zeade
(74) *Attorney, Agent, or Firm*—Berskin & Parr

(57) ABSTRACT

The invention relates to mirrors for use in confined spaces which are subject to being covered by fluids and debris, principally dental mirrors, for use by dentists and similar medical professionals. The mirror assembly includes a head portion and a handle portion. The head portion includes a housing with a rotor assembly and a rotor drive means. In accordance with the invention, a secondary member has a reflective surface. The mirror assembly includes attachment means for removably attaching the secondary member with respect to the rotor assembly so that the reflective surface can be replaced when degraded. In use, the rotor drive means spins the rotor assembly and with it the secondary member to remove fluids and debris that may fall on the reflective surface so that vision when using the reflective surface is not impaired by such fluids or debris. Advantageously the attachment means include magnetic components although mechanical attachment means may also be used. In a preferred embodiment, the handle portion includes a light source which may be moved between first and second positions for lighting the work zone of the mirror selectively as desired.

47 Claims, 11 Drawing Sheets

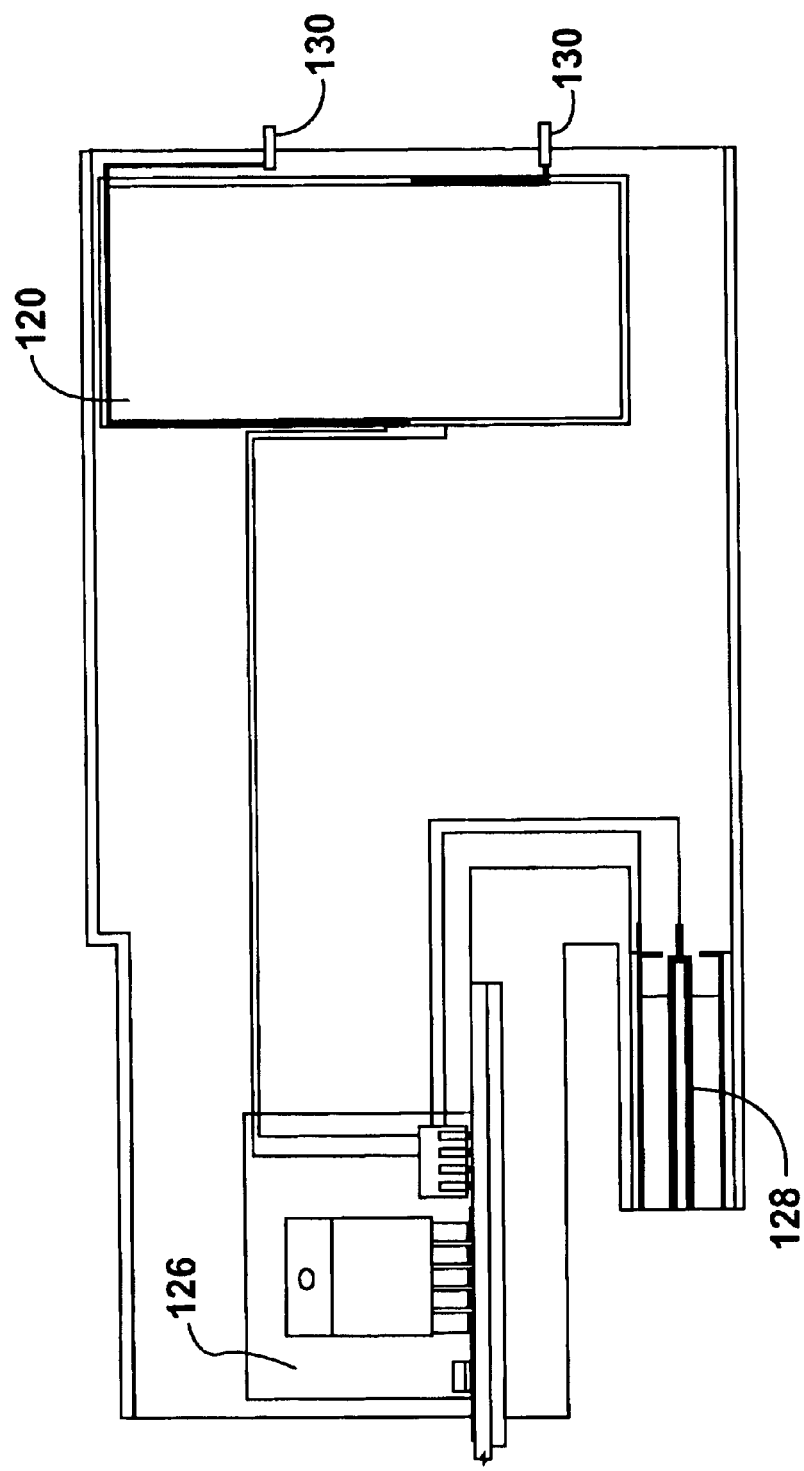

DENTAL MIRROR

FIELD OF THE INVENTION

This invention relates to mirrors used for examination of cavities such as a surgical mirror or a dental mirror having a reflective surface supported on a handle for viewing desired work sites within the cavity.

BACKGROUND OF THE INVENTION

During dental procedures it is common for dentists or other medical professionals working in the oral cavity to make use of a mirror. The mirror is usually mounted on a handle with the plane of the mirror being at an angle to the handle. The mirror is used at the same time as other dental instruments, to facilitate viewing or illumination of the work site.

While conducting appropriate medical procedures at a work site, it is often the case that various substances may fall on the reflective surface of the mirror. This may include bodily fluids originating in the cavity being worked on, cooling fluids originating from a dental hand piece or other medical instrument or other debris which maybe generated at the worksite such as cleaning grit, material removed from a tooth or bone and the like. This material generated at the worksite is often deposited on some portion of the mirror. Debris, which may be either solid or liquid, eventually blocks the operator's vision and forces the operator to frequently clean the mirror surface either by wiping it off or by having another person assisting during the medical procedures, apply fluid onto the mirror. Both of these procedures are frustrating and objectional to the medical professional.

This problem has been well recognized in the past and various attempts have been made to provide mirrors for such use which can be cleaned by various methods. In some cases the handle portion of the mirror is fitted with a suction conduit that is intended to draw debris deposited on the mirror surface, into the handle away from the mirror surface. In other cases, surfactants and anti-fogging solutions have been applied over the surface of the mirror but these are seldom suitable for handling appreciable volumes of liquids such as cooling water associated with a dental hand piece. Various forms of rinsing jets applying either water or air to the surface of the mirror have also been proposed. In some cases a brush, wiper or other cleaning surface have been included in the mirror and the brush or wiper is cycled from time to time to remove debris from the mirror.

In addition to the aforementioned approaches which have been developed to deal with this problem, another proposal is to dispel debris, whether solid or liquid, by means of centrifugal forces. This is accomplished by rotating the reflective surface so that any debris or liquid which may fall on the surface is flung from the mirror surface. In order to cause the mirror surface to rotate, it has been suggested to use some form of air turbine driven motor. An example is shown in U.S. Pat. No. 6,247,924 issued Jun. 19, 2001. This patent discloses a mirror which includes turbine blades. The turbine blades are attached to the bottom of the mirror surface and the handle is attached to a suction device which draws air into the mirror housing, past the edges of the mirror surface. The turbine blades rotate and cause the mirror surface to rotate so as to promote removal of water and other foreign substances.

Mirrors used for medical/dental purposes must be suitably disinfected before reuse on a succeeding patient. The heat and/or chemicals involved in disinfection tend to shorten the life of the mechanical features included for debris removal. Additionally, the reflective surface is subject to abrasion from the constant deposition and removal of debris and accordingly, the useful life of reflective surface is relatively short in most cases, even shorter than the mechanical components referred to above. Accordingly, all of these prior techniques have some applicability, there remains a need for alternate solutions for keeping the mirror clean using a structure with acceptable life span.

A second problem which is often associated with the use of such mirrors within cavities, arises from the need to direct light to a desired area within the cavity. In most dental suites, there is an overhead light which can be directed into the patient's oral cavity. However, a mirror is frequently used to direct the light much more precisely to a worksite which may not be illuminated directly by an overhead light. Dentists thus often use their mirror to reflect the light coming from the overhead light onto the operating site. It would be desirable that there be additional light which can be selectively directed on the reflective surface of the mirror to be reflected onto an operating site or to otherwise provide additional illumination of an operating site.

Another requirement for such devices is to enable the dentist to direct light where desired while at the same time not reflecting light back from the mirror directly into the dentist's eyes. The problem may be exacerbated as the mirror is often deployed at different angles depending upon whether the dentist is working on the upper dental arch or the lower dental arch and whether the dentist is working on the patient's right side or left side of the oral cavity.

SUMMARY OF THE INVENTION

An object of this invention is to present a device intended for use inside bodily cavities which is useful to remove debris and liquids which have been deposited on the reflective surface of a mirror.

In accordance with a first aspect of this invention a mirror assembly comprises a handle portion and a head portion. The head portion includes a housing, a rotor assembly including a rotor, and rotor drive means. The mirror assembly also includes a secondary member, the secondary member having a reflective surface. The mirror assembly also includes attachment means for removably attaching the secondary member with respect to the rotor assembly for relative rotation. The mirror assembly also includes bearing means for supporting the rotor assembly relative to the housing for relative rotation of the rotor with respect to the housing.

In accordance with a preferred aspect of the invention, the attachment means for removably attaching the secondary member with respect to the rotor assembly comprises at least one magnet component and at least one magnetic component.

In accordance with another aspect of the invention, the bearing means for supporting the rotor relative to the housing for relative rotation of the rotor with respect to the housing includes at least one ball bearing.

In accordance with another aspect of the invention, the bearing means includes at least two separate bearings and a spring means located between the bearings to axially stress the bearings.

In accordance with another aspect of the invention, a secondary member for use with a dental mirror assembly, having a rotor assembly, includes a reflective surface and the secondary member includes attachment means for removeably attaching the secondary member with respect to the rotor assembly.

In accordance with another aspect of the invention, the mirror assembly further includes at least one light source for lighting the work zone of the mirror. In a preferred embodiment of the invention, the source of light is changeable from a first position relative to the head portion, to a second position relative to the head portion wherein each of the first and second positions define a light field on either side of a lighting axis and the lighting axes of the lighting fields are at an angle to one another. In a further preferred aspect of the invention, the mirror assembly comprises a switch means for selecting functioning of the light source at the first position or the second position as desired.

In accordance with another aspect of the invention, the light source or sources may be one or more LED's. In accordance with this aspect of the invention, the invention may include cooling means for cooling the LED's.

Further and other aspects of the invention will be apparent from review of the following description of embodiments of the invention.

BRIEF DESCRIPTION OF THE DRAWINGS

A more complete understanding of the invention may be gained from review of the following illustrations of embodiments of the invention and in which:

FIG. 13 is a partial cross-sectional view of a part of the handle of the device illustrated in FIG. 1;

FIG. 15A is a top view of one of the components of FIG. 15;

FIG. 16A is a top view of one of the components of FIG. 16, and

DETAILED DESCRIPTION OF THE INVENTION

Figure 1:
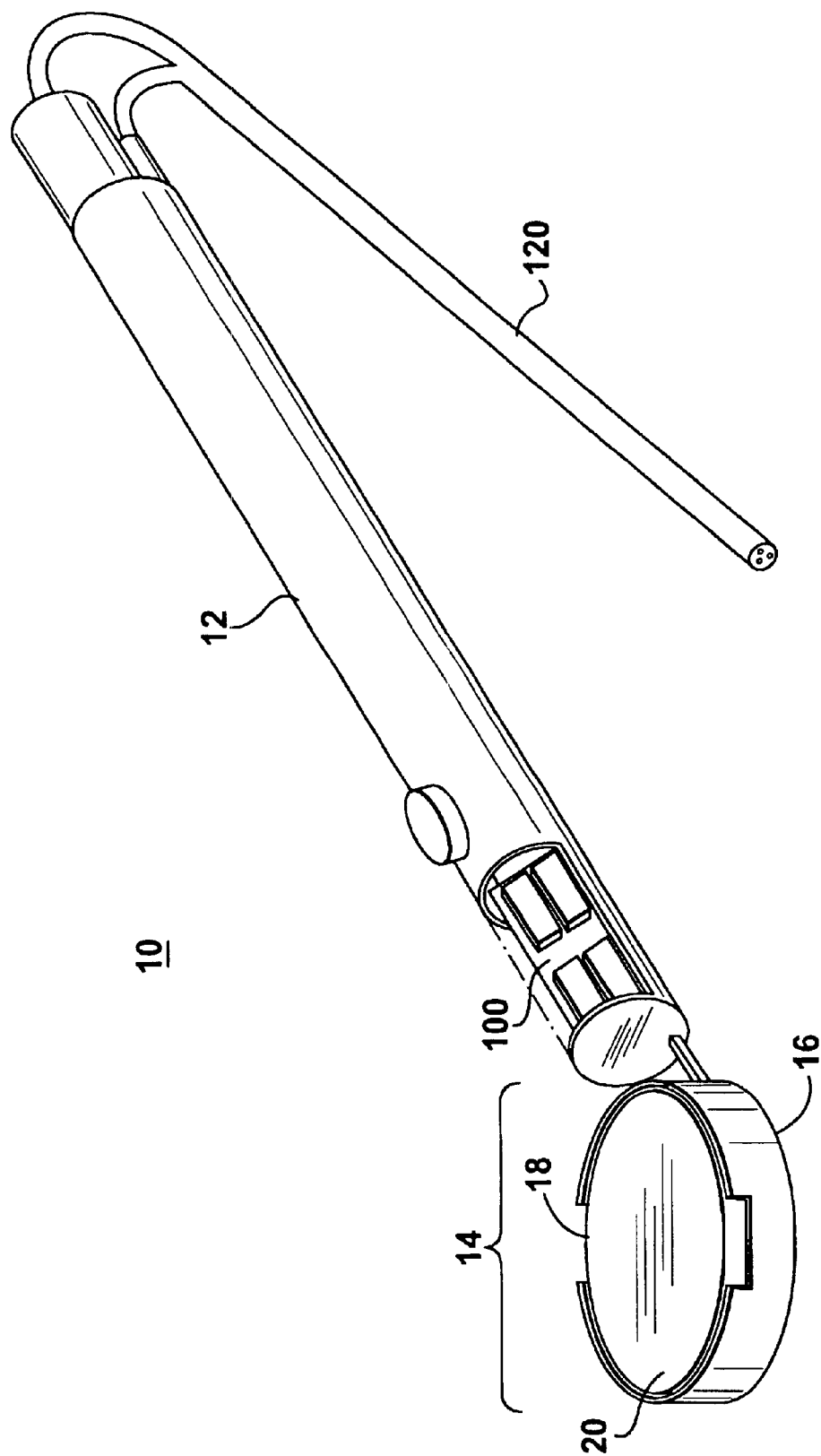
FIG. 1 is a perspective view of a mirror assembly in accordance with a first embodiment of the invention.

A first embodiment in accordance with the invention is illustrated in FIG. 1. The embodiment illustrated in this figure is a dental mirror assembly for use by dentists in performing typical dental procedures within a patient's oral cavity. The dental mirror assembly is illustrated generally at 10. The dental mirror assembly 10 includes a handle portion 12 and a head portion 14. The head portion 14 is attached to the handle portion structurally to enable the dentist to maneuver the head portion by manipulating the handle portion 12. In addition, the structural connection between the head portion 14 and the handle portion 12 may include conduits for communicating electrical wires and in addition fluids, all as more fully explained below.

Figure 2:
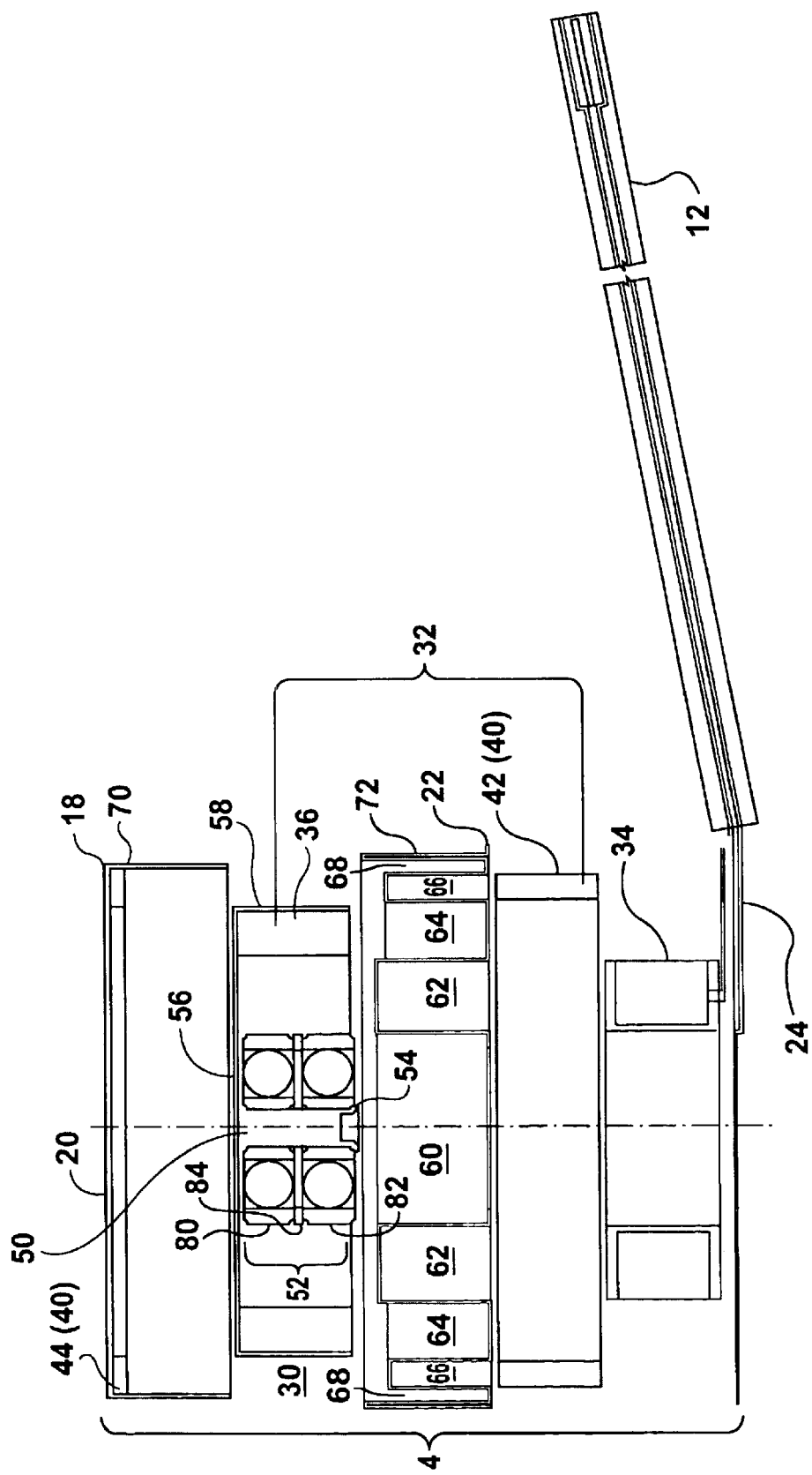
FIG. 2 is an exploded assembly view, in section, of the mirror assembly of FIG. 1.

As illustrated in FIGS. 1 and 2, the head portion 14 includes a housing 16 and a secondary member 18. The secondary member 18 includes a reflective surface 20. The housing 16 comprises an upper shell 22 and a lower shell 24. The housing 16 houses a rotor assembly 30. The housing also includes rotor drive means 32 which includes a coil assembly 34 and a drive magnet 36.

The head portion also includes attachment means indicated generally at 40, which in the embodiment illustrated in FIGS. 1 and 2, include a magnet component 42 and a magnetic component 44. In this disclosure and claims, the terms "magnet component" and "magnetic component" are used to refer to devices which create therebetween a magnetic attraction. At least one of the devices is a magnet. The other of the devices may be a magnet or may be any other material which is magnetically attracted to a magnet, such as a ferrous material or the like. Thus, the term "magnetic component" is intended to be broad enough to cover any structure which is attracted to a magnet. The term "magnet component" is intended to be broad enough to apply to any structure which develops magnetic forces. These may include permanent magnets as well as electric devices which create a magnetic field when energized, such as a coil or solenoid or the like. As shown in FIG. 2, preferably the magnet component 42 is a solenoid which can be energized or de-energized as desired. For economic reasons, the magnetic component 44 as illustrated in FIG. 2 is preferably a torroidal shaped magnetic component which may simply be a ferromagnetic ring.

The rotor assembly 30 as illustrated in FIG. 2 includes a rotor shaft 50, a bearing assembly 52 and a bearing retainer 54. The rotor assembly 30 may also include a generally planar rotating plate 56 which is attached to the shaft 50 and a depending wall 58 which depends from the plate 56. The depending wall 58 is a cylindrical wall and the plate 56 may be a circular plate.

As shown in FIG. 2, the head portion 14 is assembled by moving the components illustrated in FIG. 2, toward the lower shell 24. In order to accommodate the various components as outlined above, the upper shell 22 contains a number of open sided compartment areas. With reference to FIG. 2, there is a central compartment 60, a first radially outwardly torroidal compartment 62, a second radially outwardly torroidal compartment 64, a third radially outwardly torroidal compartment 66, and a fourth radially outwardly torroidal compartment 68.

Upon assembly, the coil assembly 34 is received within the first radial torroidal compartment 62. The drive magnet 36 and the depending wall 58 are received within second radially outer torroidal compartment 64. In addition, the magnet component 42 which is preferably in the form of a solenoid is received within the third radially outward toroidal compartment 66. The bearing assembly 52 is received within the central compartment. The bearing assembly may be press fit into the upper shell 22. Alternate means to retain the bearing assembly may include mechanical fixation such as an additional retainer or adhesives such as the high temperature adhesive available from ARALDITE™. When the housing 16 is assembled, the upper shell and the lower shell are welded together by laser or diffusion welding around the outer and inner perimeters and along the orthogonal extension so that upon assembly the coil assembly of the rotor drive means and the magnet component for retaining the secondary member are sealed within a closed chamber. The head portion can then be autoclaved between uses as required for typical sterilization procedures. The upper and lower shells may be made from metal or other heat weldable autoclaveable materials including plastics.

The secondary member 18 includes the reflective surface 20 as well as a cylindrical depending wall 70, the reflective surface being circular when viewed from above. At the intersection of the underside of the reflective surface 20 and the depending wall 70 there is located an area to accommodation the magnetic component 44, which as previously indicated, may be in the form of a ferromagnetic ring. With this arrangement, the secondary member 18 comprises a cap-like structure. On assembly of the secondary component 18 to the housing 16, the depending wall 70 is received within the fourth radially outwardly torroidal compartment 68. As shown in FIG. 2, the magnetic component 44 is located immediately above the magnet component 42. Upon energizing the magnet component 42, the magnetic component 44 is attracted and the reflective surface is then held closely adjacent the plate 46 of the rotor assembly 30.

When the rotor drive means is energized the rotor assembly 30 spins, being driven relative to the housing 16. Because the secondary member is magnetically attracted to the magnetic component 42, the secondary member 18 spins with the rotor. It is this spinning action, which discharges from the reflective surface 20, any solid or fluid debris which may become deposited on the reflective surface 20 during the dental procedure. The rate of spin can be controlled by the magnetic forces generated by the rotor drive means 32. Generally, however, the rotor should spin at a speed of about 5,000 rpm or higher. This assures acceptable cleaning of the reflective surface.

One of the principal advantages of the magnetic interaction of the attachment means 40 is that the secondary member 18 can be readily detached from the housing 16. This is achieved by turning off the current to the magnet component 42. When the magnet component 42 is de-energized, the secondary member can be easily removed from the mirror assembly to facilitate replacement of the secondary component 18. The reflective surface 20 of the secondary component typically becomes marred after relatively few patients, from the debris which impacts onto that surface and possible contact with other dental equipment being handled by the dentist or dental assistant. As that reflective surface deteriorates, the quality of the mirror becomes less satisfactory. The system described herein facilitates replacement of the reflective surface. All that must be changed is the secondary member 18. The rotor assembly 30 need not be disassembled from the housing 16. After what may be a relatively short life span, a replacement secondary member can be easily installed.

The secondary member 18 will be rotating relatively rapidly along with the rotor assembly 30. It is desirable that the rotating rotor assembly and secondary member do not contact any of the patient's bodily surface or other dental instruments. Accordingly, the depending wall 70 of the secondary member 18 is located radially inwardly from the upstanding radial wall 72 of the upper shell 22. The upper shell 22 does not rotate and thus rotating components of the rotor assembly and secondary member 18 are shielded from contacting the patient's tissue by the wall 72. Thus, the diameter of the first wall 70 is less than the diameter of the second wall 72. The depending wall 70 is closely received within the torroidal compartment 668. Thus a safety feature. The secondary member cannot move radially when so confined. Accordingly, the secondary member can be removed from the rotor assembly 30 only by moving axially. This reduces the chances of inadvertent removal if the secondary member 18 is contacted by a hit by any other apparatus being used by the dentist or dental assistant.

The rotor assembly 30 advantageously includes a first ball bearing 80, a second ball bearing 82 and a spring washer 84. In order to provide a satisfactory viewing surface for the reflective surface 20, when that surface is revolving at high speed, it is desirable that there be a minimum amount of wobble in that surface. Any wobble in the reflective surface tends to degrade the effect of the mirror. While a single bearing supporting the shaft 50 is marginally acceptable, it has been discovered that much improved mounting of the rotor assembly to minimize wobble can be achieved by providing more than one bearing. The ball bearings 80 and 82 are high quality bearings. A suitable example is the model UL 103 ball bearing available from RMB Roulements Miniatures S.A. However, increased stability is achieved using a spring washer 84. The ball bearings include an inner race which is adjacent to the shaft of the rotor and an outer race which is adjacent to the rotor drive means. The spring washer is positioned between the outer races of the first and second ball bearings. The spring washer 84 axially loads the bearings in a direction parallel to the axis of the shaft 50. Thus, the bearing retainer 54 captures the bearings between the retainer 54 and the plate 56 of the rotor assembly 30. The bearing retainer bears against the inner race of the ball bearing adjacent the retainer. By spring loading the outer race of the two bearings in the axial direction, it has been possible to provide a minimum of deflection of the rotor as it revolves. As the secondary member 18 is held onto the rotor by magnetic attraction, the secondary member is also stabilized by the well supported rotor, thereby minimizing deflection of the reflective surface 20 and any consequent degradation of the quality of the reflected image during rotation.

Figure 3:
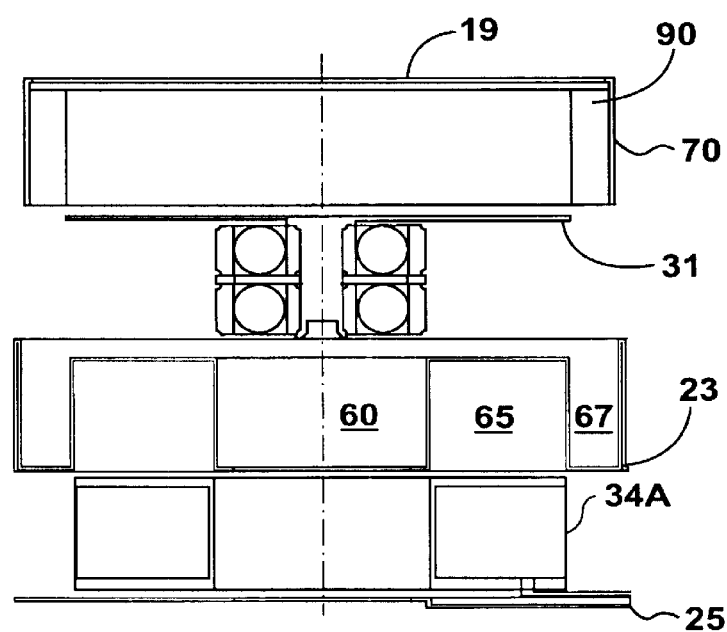
FIG. 3 is a view similar to FIG. 2 illustrating alternate embodiment for a portion for the mirror assembly of FIG. 1.

FIG. 3 illustrates an embodiment of the invention which is slightly different from the embodiment illustrated in FIG. 2. In this embodiment, the head portion 14 includes a lower shell 25, an upper shell 23 and a secondary member 19 as well as a rotor assembly 31. In this embodiment of the invention, the upper shell 23 includes a central compartment 60 for receiving the bearing assembly 52 of the rotor assembly 31. The upper shell 23 also includes a first radially outer torroidal compartment 65 and a second radially outwardly torroidal compartment 67. In this embodiment, the rotor assembly 31 includes a plate 56 but does not include the downwardly depending wall 58 shown in FIG. 2. The secondary member 19 includes a multi-polar magnet assembly 90 which is adjacent to the depending wall 70 of secondary member 19. In this embodiment, the lower shell 25 includes a rotor drive coil 34A and a ferromagnetic portion at its radially outward portion that will be aligned with the multi-polar magnet assembly 90. In this version, the secondary member 19 is held in place by the axial attraction forces between the coil assembly 34A and the multi-polar magnet 90 as well as between the multi-polar magnet 90 and the ferromagnetic structure of the lower shell 25.

It has been observed that during sterilization, particularly by autoclaving, magnetic materials slowly demagnetize. Accordingly, to promote a longer sterilizable life for the motor, the magnetic components illustrated in FIG. 2, in particular drive magnet 36, are made of a more expensive magnet material such as samarium cobalt. This permits repeated autoclaving. One of the advantages achieved by the embodiment depicted in FIG. 3 is that the multi polar magnet 90 is part of the secondary member 18 which is intended to be replaced after twenty to thirty cycles of autoclaving. Therefore, the multi polar magnet 90 can be made of a less expensive material such as plastic bonded nickel boron or ferrite. In the structure illustrated in FIG. 2, repeated autoclaving will shorten the life of the drive magnet component 36 more than it will effect the other parts of the motor such as the bearing assembly 52, the coil 34 and the shells 22 and 24. Thus, replacement of the mirror assembly will be determined by the life of the drive magnet 36. In the structure shown in FIG. 3, because the magnet component 90 is part of the replaceable secondary member 19, there will be a longer useful life for the shells, coil and bearing assembly.

Figure 4:
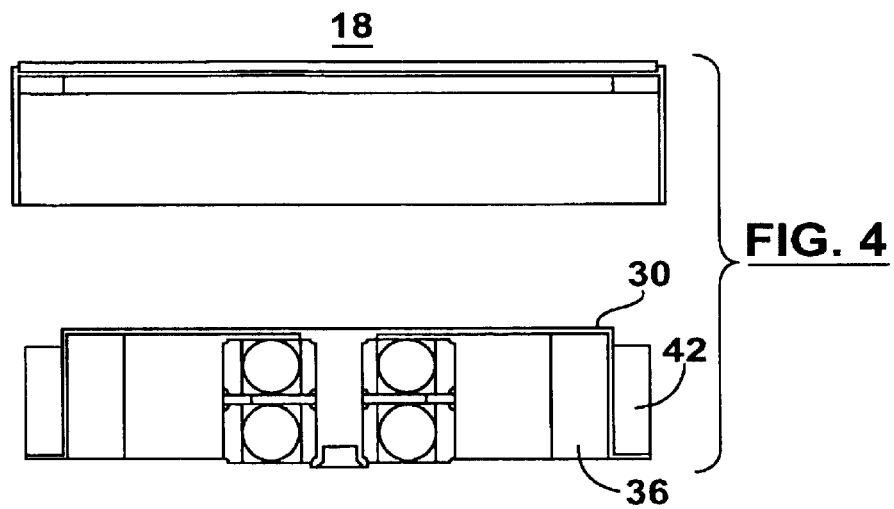
FIG. 4 illustrates a further alternate embodiment of a portion of the mirror assembly of FIG. 1.
Figure 5:
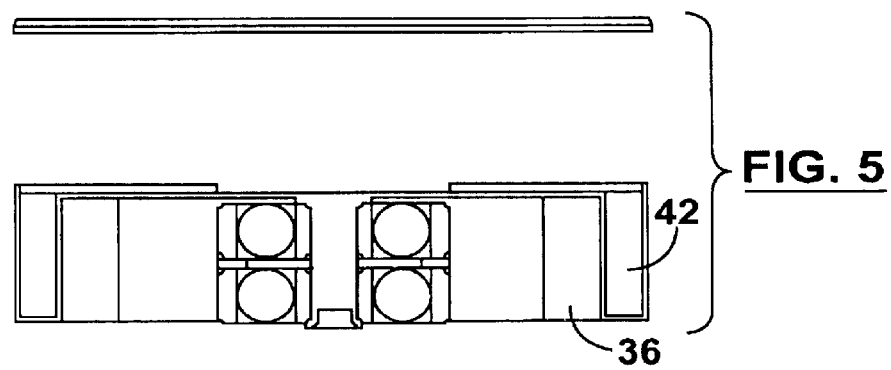
FIG. 5 illustrates a further alternate embodiment of a portion of the mirror assembly of FIG. 1.

FIG. 4 and FIG. 5 illustrate alternate embodiments for the attachment means for the rotor assembly 30 and the secondary member 18. In FIGS. 4 and 5, a magnet component 42 is attached to the rotor assembly 30. The embodiments shown in FIGS. 4 and 5 result in a somewhat heavier rotor. This added weight may require a slightly higher motor power. In the embodiment of FIG. 4, the secondary member 18 is substantially similar to that depicted in FIG. 2. In FIG. 5, the secondary member 18 is an essentially planar member without a downwardly depending wall 70 as illustrated in FIG. 2. In this case the secondary member 18 can be made from a magnetic or ferromagnetic disk with a deposited or bonded mirror layer on the upper surface layer thereof. The advantage of the secondary member 18 illustrated in FIG. 5, however, is that without the need for creating the depending wall 70, the secondary member may be relatively inexpensively manufactured.

Figure 6:
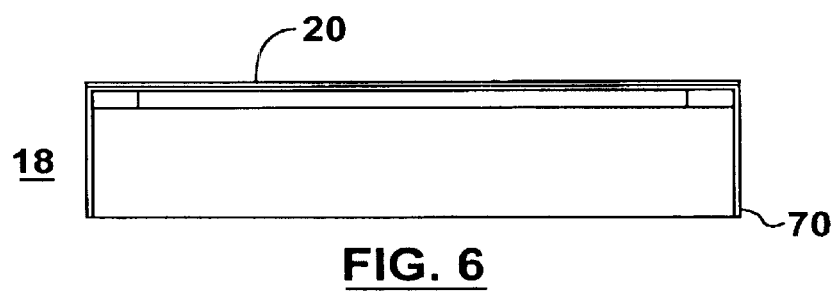
FIG. 6 illustrates in cross-section, further alternate embodiment of a portion of the mirror assembly of FIG. 1.
Figure 7:
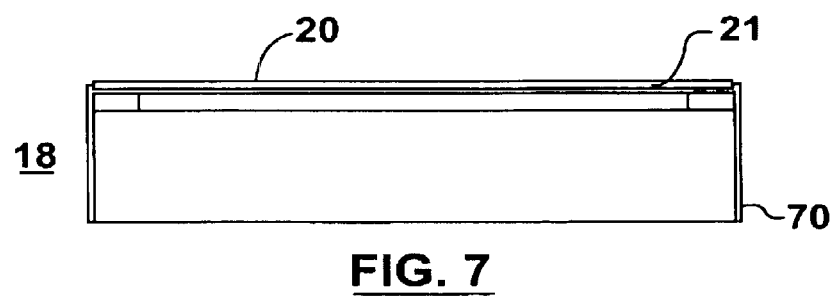
FIG. 7 is a view similar to FIG. 6 illustrating an alternate embodiment for that component.

FIGS. 6 and 7 illustrate other embodiments of the secondary member 18. In FIG. 6, the reflective surface 20 is deposited directly on top of the material which forms the secondary member 18, while in FIG. 7, the reflective surface 20 is deposited on a substrate 21 which may be made of glass, plastic or metal which is initially separate from the remainder of the secondary member 18 and is joined thereto after creation of the reflective surface.

In the above embodiments, the rotor drive means has been described in the context of an electrical motor. The preferred electrical motor is what is referred to as a brushless motor. An example of such a brushless motor is the motor which is part of fan model KF0306BDM available from JAMICON®. The brushless motor is relatively small in the axial direction and thus allows the axial thickness of the mirror assembly to be minimized as much as possible.

Figure 9:
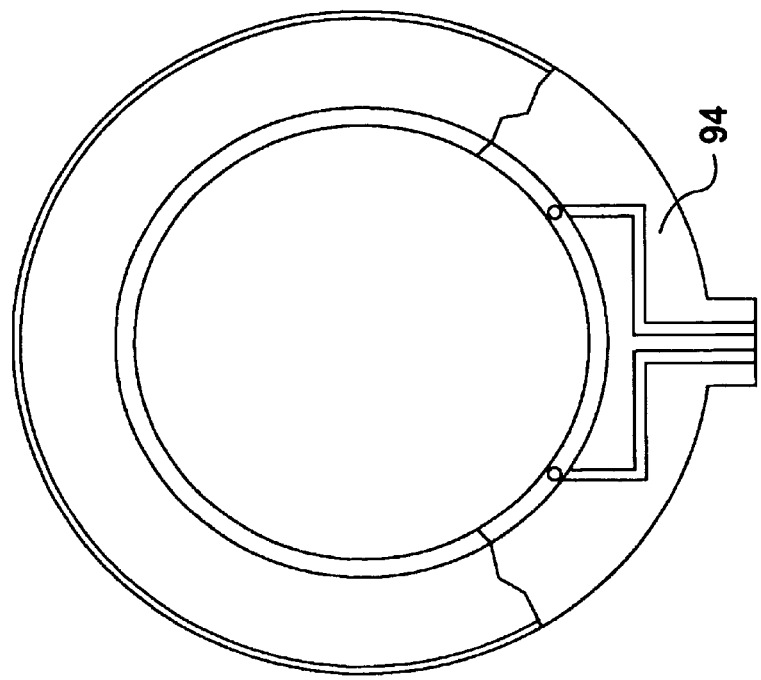
FIG. 9 is a top sectional view of the structure of FIG. 8.
Figure 8:
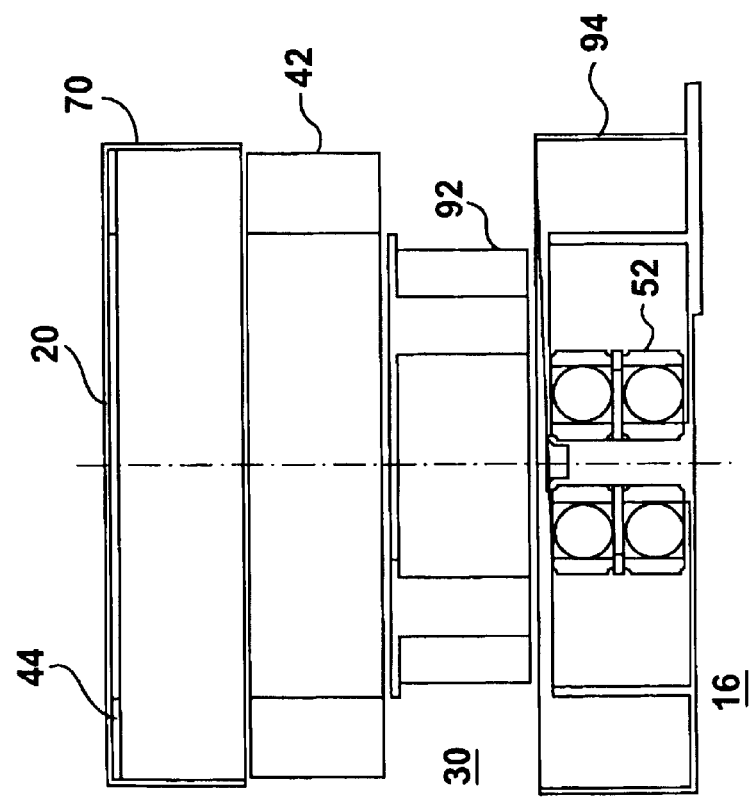
FIG. 8 illustrates an alternate rotor drive system for use with a portion of the embodiment illustrated in FIG. 1.

As an alternative to using electrically driven motors, the rotor assembly 30 may be driven by a fluid turbine. Advantageously, placing the bearing assembly 52 toward the inside of the turbine will reduce the overall diametrical size of the turbine drive system. A turbine drive system is shown in FIGS. 8 and 9. In this case, the housing 16 includes a radially outer case 94. The case 94 delivers a fluid which may be either liquid or gaseous, to a turbine impeller 92 which is part of the rotor assembly 30. Typically a source of pressurized fluid as may be available in most dental units is used to supply fluid under pressure. The fluid is delivered to the case 94 and then through suitable ducting to impact upon the vanes of the impeller 92 causing the rotor assembly to rotate. Also, bearing assemblies 52 as previously discussed may be used in association with the rotor. Similarly, similar magnetic means form the attachment means for holding a secondary member 18 on the turbine 92. This type of dental mirror requires a connection between the handle portion 12 of the mirror assembly 10 and a dental unit so that the mirror assembly can be supplied with air or water to drive the turbine. Although it may be most convenient to connect this to an existing dental unit any other source of pressurized fluid available at the dental theatre may be utilized for this purpose.

In accordance with another aspect of the invention, the dental mirror 10 includes at least one light source for lighting the work zone of the mirror. The term "work zone of the mirror" is used throughout this description and in the claims to describe either the reflective surface of the mirror itself or the area of the patient's body adjacent to which the mirror is being positioned. Generally the work zone is located within about 0.5 to 5 cm of the reflective surface. In some cases, it will be desirable to have a light source directed toward the reflective surface to be bounced from the reflective surface to a portion of the oral cavity where the dental procedure is being carried out. In other circumstances it will be desirable to illuminate the site where the dental procedure is being carried out, directly, that is, without the light first being reflected from the reflective surface. In this latter case, the dentist can use the mirror to view the desired site for the dental procedure which is lit directly. In the former case, the dentist may use the mirror to light the site of the dental procedure while viewing the site directly.

Figure 10:
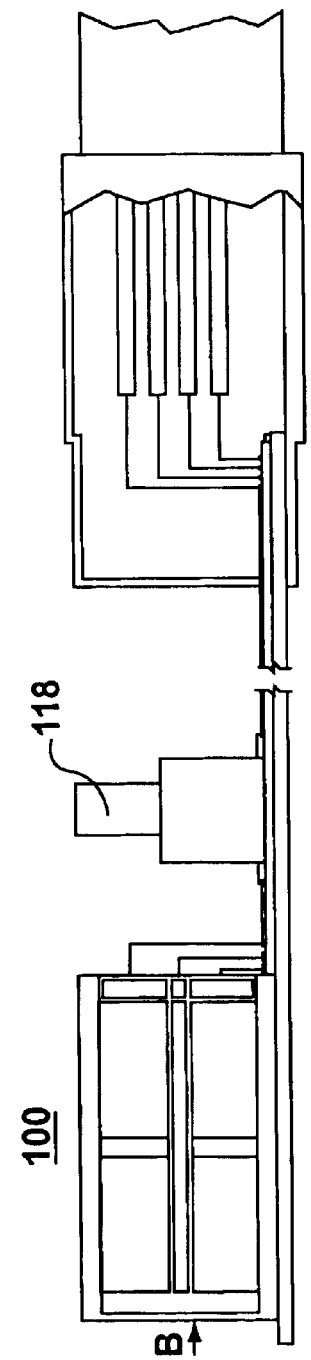
FIG. 10 is a partial cross-sectional view through the handle portion of the embodiment illustrated in FIG. 1.

The dental mirror assembly of the embodiment illustrated in FIG. 10 involves a handle portion 12 which is normally at an obtuse angle to the reflective surface 20. That particular angle is chosen to enable the dentist to position the mirror as desired. However, the operating site for the dental procedure may be on either side of the handle of the mirror and will change depending upon whether the dentist is working on the upper or lower dental arch and whether working on the left or right hand side of the patient's oral cavity. This will also switch if the dentist happens to be left handed. Accordingly, in a preferred embodiment of the invention illustrated in accordance with this aspect of the invention, means are provided to alternately light particular areas. In this disclosure and claims, the light emanating from a light source is described as being a "light field". This light field lies on either side of a "lighting axis". The "lighting axis" emanates from the position where the light leaves the light source. In the preferred embodiment of the invention there are at least two light fields and the lighting axes are at an angle to one another. Preferably the mirror assembly includes a switch means for activating one or the other of the light fields so that the dentist can selectively use one of the two light sources. This means that as the dentist moves within the patient's dental arch from left to right or from the upper arch to the lower dental arch, the dentist can select the light field which achieves the desired purpose. By selecting the desired light field the "user" can minimize undesirable reflections of light back to the user and avoid direct light being directed toward the user.

A preferred source of light is an LED. While a single LED can be used to create a light field, two or more individual LED's placed adjacent one another, may be used to constitute a single light field.

FIG. 1 illustrates the handle portion 12 of the dental mirror 10. The handle portion 12 includes an illuminator assembly indicated generally at 100. The illuminator assembly is located substantially adjacent the end of the handle portion 12 which is next adjacent to the head portion 14. The exact size and orientation of the illuminator assembly may be varied as desired.

Figure 12:
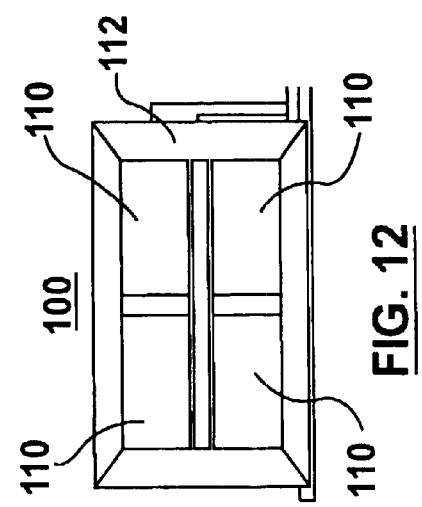
FIG. 12 is a view of the component shown in FIG. 11 in the direction of arrow A of FIG. 11.
Figure 11:
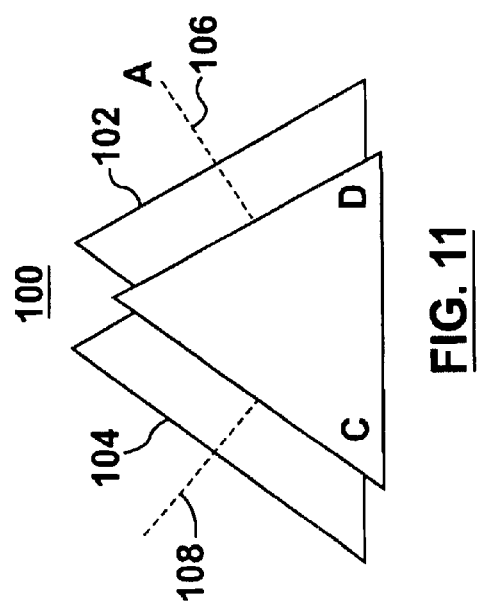
FIG. 11 is a view of the structure shown in FIG. 10 in the direction of arrow B of FIG. 10.

FIGS. 10, 11 and 12 schematically illustrate the illuminator assembly 100 as shown in FIG. 1 together with its operating controls which are within the handle portion 12. FIG. 10 is a schematic view taken of the handle portion 12 in cross section. FIG. 11 is an end view of the illuminator assembly 100 of FIG. 10 taken in the direction of arrow B. FIG. 12 is a view of the illuminator assembly 100 of FIG. 11 taken in the direction of arrow A.

The illuminator assembly 100 includes a first light field 102 and a second light field 104. The first light field 102 comprises a lighting axis 106 while the second light field 104 comprises a lighting axis 108. The lighting axis 106 and 104 respectively are shown as dotted lines. Those dotted lines 106 and 104 show that the lighting axes of the two lighting fields 102 and 104, intersect at an angle. Preferably as shown in FIG. 11, the lighting fields 102 and 104 do not overlap to any substantial extent thus providing for mutually exclusive lighting fields. Each lighting field is independent from one another so that the first and second lighting fields may be operated individually.

As is shown in FIG. 12, the lighting field 102 is made up of four individual LED's 110. The four LED's are included in a lighting array which is within a trough 112. The trough 112 acts as a reflector to direct the light emitted from the LED's 110 outwardly to form the desired light field 102. The LED's 110 are preferably white. Examples of LED's which may be conveniently used include the LUXEON® emitter model LXHL-BW01 from LUMILEDS™ Lighting LLC. Four LED's have been shown in this embodiment, either more or fewer LED's may be used to provide the desired output. It is believed that the most desired light flux around each light field will be between 10 and 30 lumens.

As shown in FIG. 11, the two light fields 102 and 104 emanate from a substantially triangular cross sectional shaped portion of the handle 12. As shown in FIG. 11, the triangular section need not have the same angles C and D. Thus, the lighting emanating from either side of the section may be directed at any angle as chosen by the designer if any special needs for the dentist will be required.

Preferably, the handle portion 12 includes a switch 118 to control the operating of the light sources producing the light fields 102 and 104. The switch may be a simple cycle switch with a separate switch providing an on/off function for the current supplied to the light source(s). Alternatively, the switch 10 may cycle through several different functions from, first light field on, to second light field on, to off, or any other combination of functions as may be desired.

If LED's are selected as the illumination source as illustrated in this embodiment, the LED's will typically be powered from a suitable control board which will be contained within the handle portion 12. The power for the LED's may be generated from a battery also mounted within the handle portion 12 of the mirror assembly 10, or alternatively, from an exterior source in which case some type of umbilical conduit 120 as shown in FIG. 1 will be required. The umbilical conduit 120 may deliver electrical power for the LED's, electrical power for the electric motor if one is used, or fluid under pressure if a turbine motor is used to operate the rotor drive means.

Typically when LED's are used as a lighting source, consideration must be given to cooling requirements. The umbilical conduit 120 may also include a source of fluid which can be delivered as necessary to provide the appropriate cooling. The cooling fluids supplied through the umbilical conduit 120 can circulate as required through the handle portion 12 to cool the control board if necessary, and more importantly, to supply cooling directly to the vicinity of the LED's. For this reason, the LED array to each of the first and second lighting fields 102 and 104 may include a heat sink. The heat sink may be included within the triangular section (see FIG. 11), where there can be accommodated a supply and return flow passage to provide adequate cooling for the heat sink(s). Various forms of heat sink may be provided. Where desirable, the handle portion 12 may include a suitable cooling structure which acts as a heat sink. This may be made from metal or other substance which is a good thermal conductor. This structure would then be used to conduct heat away from the LED's or the heat sink. Advantageously, heat may be conducted away from the LED assembly using a heat pipe. Such heat pipes are available commercially. One example is the 3 mm diameter heat pipe available from AVC Asia Vital Components Ltd.

FIG. 13 schematically illustrates in longitudinal cross section, the handle portion of a self-contained or cordless dental mirror 10. The dental mirror assembly 100 includes a rechargeable battery 120 and a controller 126. The controller 126 includes a rotor drive means connector 128.

The controller 126 receives power from the battery 120. That power may then be directed by the controller through suitable circuitry to power the light sources as desired as well as to deliver power to the motor for rotation of the reflective surface of the dental mirror assembly. The connector 128 may also be useful for operating the solenoid for retaining the secondary member 18 with respect to the housing 16.

When the unit has been used for a sufficient period of time, the unit can be returned to a recharge/recycle station. When at that station, the battery may be recharged through connectors 130.

This dental mirror assembly 100 provides a cordless mirror assembly as an alternative to the embodiment illustrated in FIG. 1 which uses an umbilical connection for supply of needed electricity. Because of the need to provide a battery within the handle, the cordless unit will have a larger handle. The cordless model can be used anywhere and does not require the use of an umbilical cord. On the other hand, the device as shown in FIG. 1 with an umbilical cord can be made smaller and more compact, but of course can be used only in association within the length of the umbilical connector.

In the embodiments described hereinbefore, the reflective surface of the secondary member 18 is shown as being affixed to the rotor assembly by means of a magnetic connection. While the magnetic connection has certain desirable features, including the ability to attach and remove the secondary member from the rotor assembly without tools, it is considered within the scope of this invention to utilize mechanical connection between the secondary member and the rotor assembly.

Figure 14:
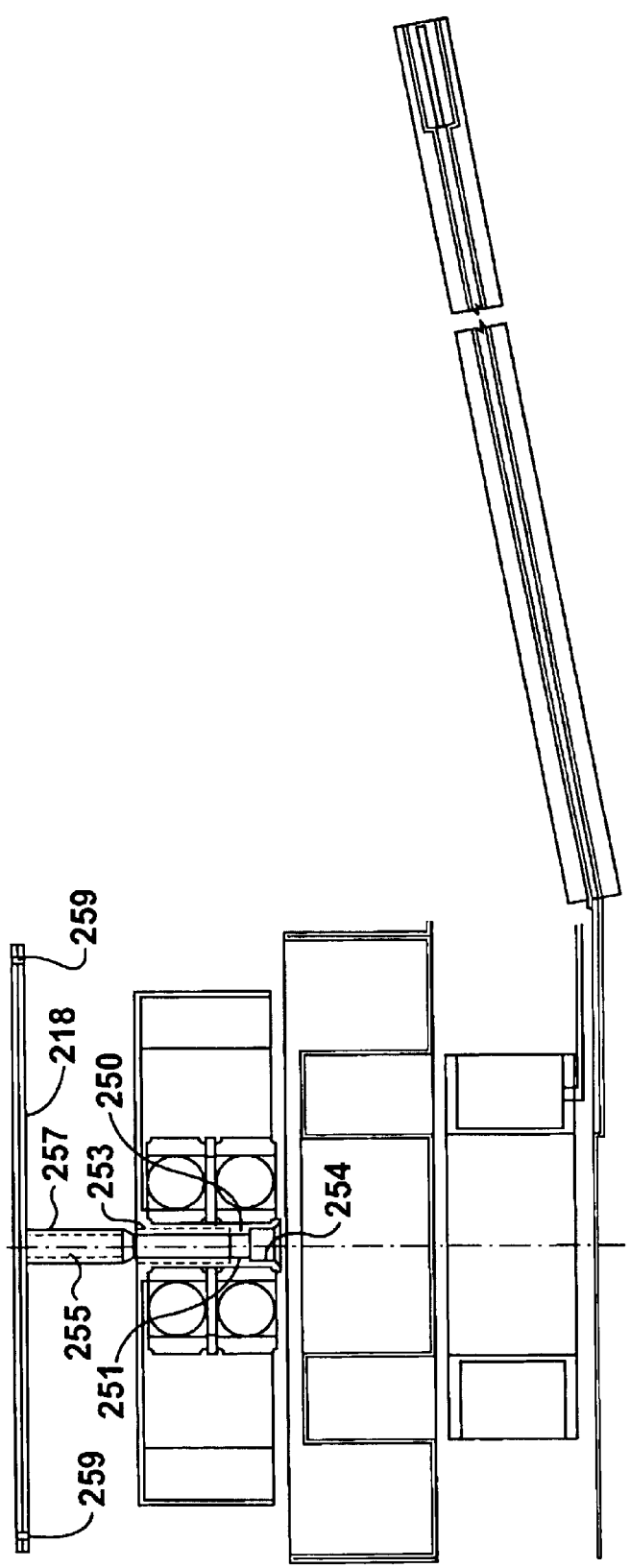
FIG. 14 is a view similar to FIG. 4 illustrating an alternate attachment mechanism for two of the components.

One such mechanical connection is illustrated in FIG. 14. In FIG. 14, the rotor shaft 250 is hollow and contains a central bore 251 containing a thread 253. The secondary member 218 includes a shaft 255 having an external thread 257. The shaft 255 can be inserted into the hollow shaft 250 with the threads 257 of the shaft 255 engaging the internal threads 253 of the shaft 250. In this case, the secondary member 218 includes a generally planar surface to which the reflective surface is attached. The reflective surface may be attached by deposition or be a separate substrate glued or otherwise adhered to the planar surface attached to shaft 255 or the reflective surface may be polished or otherwise created directly on the planar surface.

The bearing retainer 254 includes a socket to accept a first tool. Any type of tool and socket arrangement may be used. The secondary member 218 includes a pair of small holes 259 which are intended to receive projecting dowels from a second tool. In order to assemble the secondary member 218 to the rotor assembly 230, a first tool having a projecting insert is placed into the mating socket of the shaft 250. The shaft is then immobilized by grasping the tool and the secondary member may be threaded into the bore 251. In order to rotate the secondary member, the second tool having a pair of dowels spaced to be received within the holes 259 may be used to rotate the secondary member 218 so that the secondary member 218 can be rotated relative to the shaft 250 until the threads bottom out.

Figure 15:
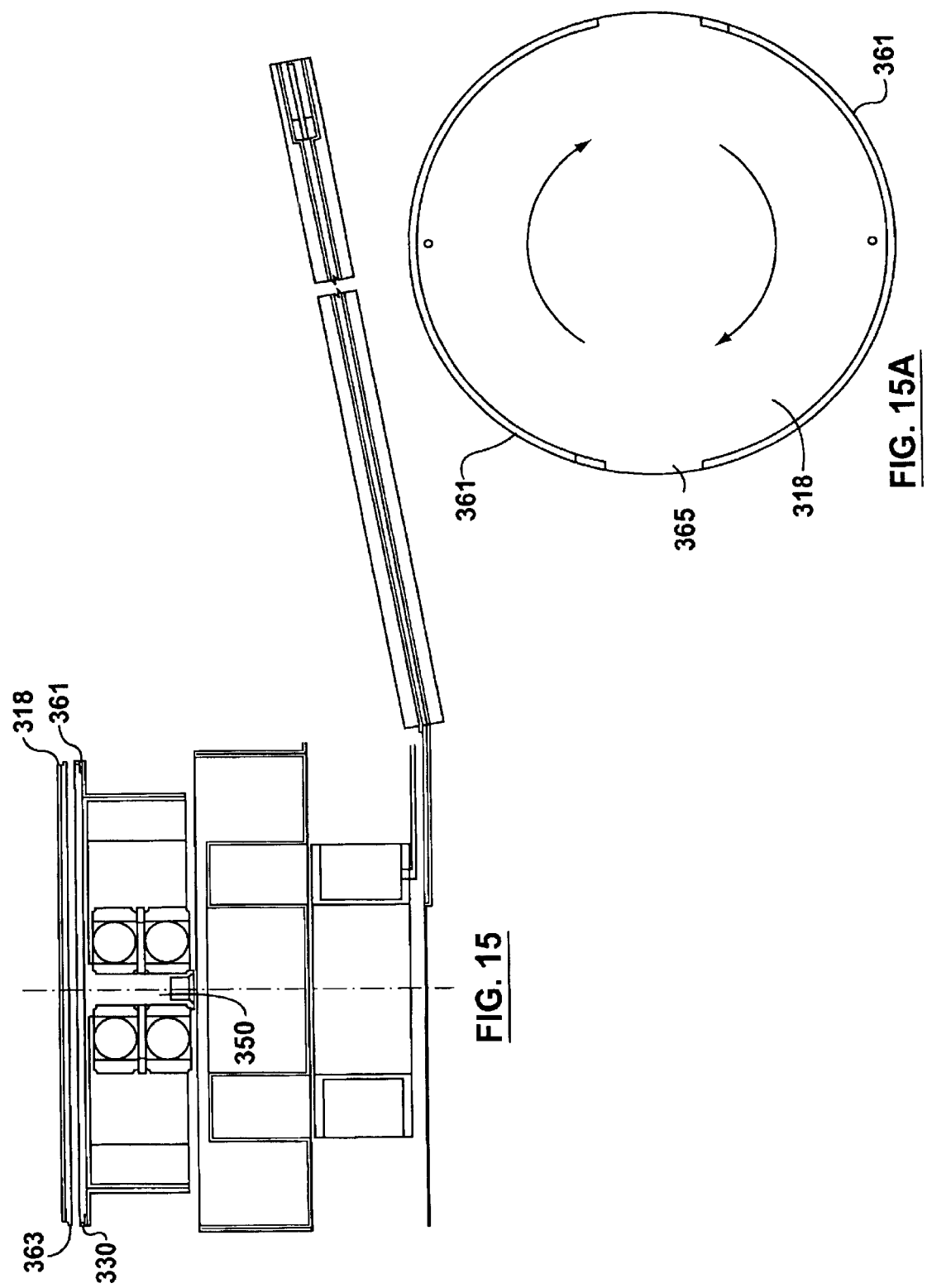
FIG. 15 is a view similar to FIG. 14 illustrating a further alternative embodiment for attaching certain components.

FIG. 15 illustrates an alternate mechanical system for attaching a secondary member 318 to a rotor assembly 330. In this case, the rotor assembly 330 includes a substantially planar surface extending perpendicular to the axis of the shaft 350. Peripherally arranged about the circumference of the planar surface there is an upstanding lip 361. The secondary member 318 includes a plurality of outstanding tangs 363. The tangs 363 project into slots 365 in the upstanding rim 361 to permit vertical assembly (as shown in FIG. 15) of the secondary member 318 into the planar member of the rotor assembly. Once the tangs 363 are received within the slots 365 the secondary member is rotated so that the tangs 363 no longer are aligned with the slots 365.

Figure 16:
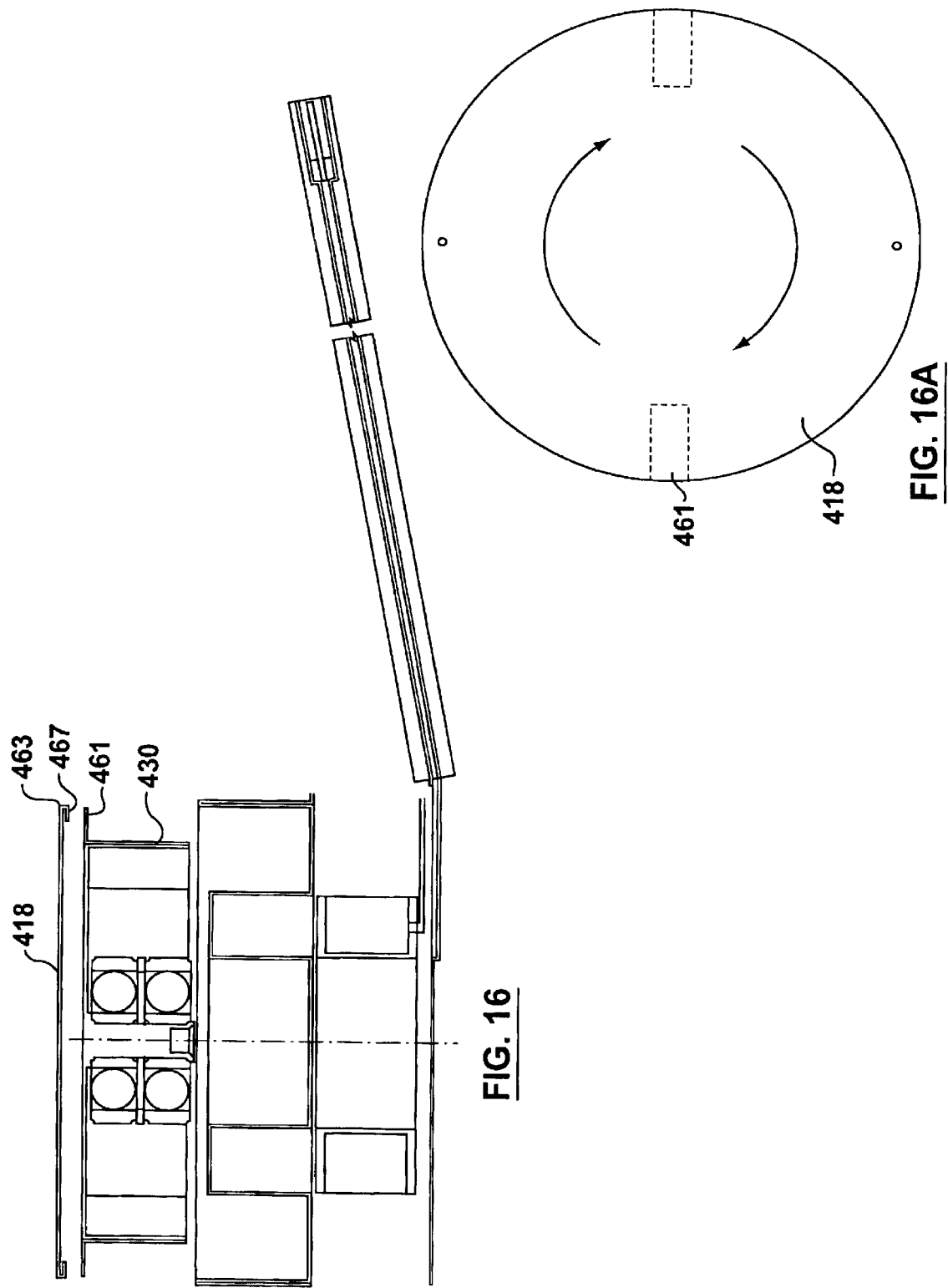
FIG. 16 is a view similar to FIG. 14 illustrating a further embodiment for attachment of certain components.

A somewhat similar system is illustrated in FIG. 16. In this case, the secondary member 418 includes a downwardly extending lip 463 with tangs 467. The rotor assembly 430 includes a planar surface which advantageously includes a plurality of slots 461. The slots are dimensioned to receive the tangs 467. Again, assembly is achieved by moving the secondary member 418 against the rotor assembly 430 with the tangs 467 aligned with the slots 461. The secondary member 418 is then rotated so that the tangs 467 no longer align with the slots 461.

In the structures illustrated in FIGS. 15 and 16, advantageously, the bearing retainer includes a socket for receiving a tool so that the shaft of the bearing assembly may be immobilized while the corresponding secondary member is rotated. In order to facilitate rotation of the secondary member it may be provided with a pair of holes to receive a tool having a corresponding set of dowels as explained in connection with the structure illustrated in FIG. 14.

Figure 17:
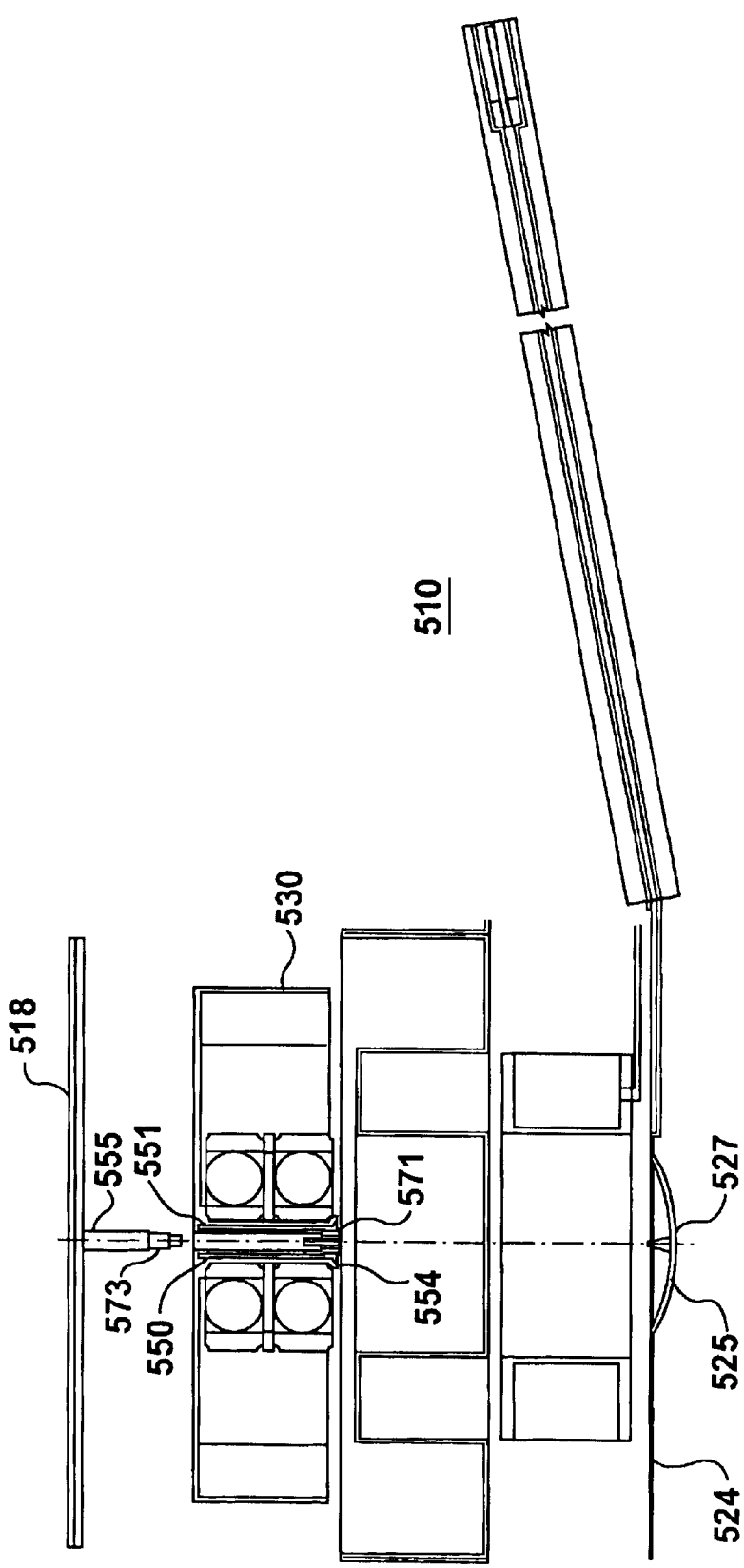
FIG. 17 is a view similar to FIG. 14 showing a further alternate embodiment for attaching certain components.

FIG. 17 illustrates a further embodiment utilizing a mechanical retention means for retaining a secondary member 518. In this structure, the secondary member 518 includes a shaft 555. The shaft 550 of the rotor assembly 530 is hollow and contains a bore 551. In this case the bearing retainer 554 includes a chuck 571. The shaft 555 of the secondary member 518 includes an end fitting 573 which is adapted to be received within the chuck 571.

In the structure indicated in FIG. 17, the lower shell 524 includes a centrally directed outwardly bowed spring bottom portion 525. When the dental mirror 510 is assembled, the bearing retainer 554 is substantially adjacent the spring bottom portion 525. Advantageously, the spring bottom portion 525 may have an upwardly projecting finger 527. The finger 527 can be moved upwardly toward the rotor assembly 530 by pressing the spring bottom upwardly. On doing so, the finger 527 contacts the lower surface of the chuck 571. Upward movement of the chuck 571 then opens the fingers of the chuck. With the fingers of the chuck open, then the secondary member 518 can be moved toward the lower shell until such time as the end portion 573 is received within the chuck 571. When the secondary member 518 has been correctly positioned, the spring bottom is released. This removes the finger 527 from the chuck 571 so that the chuck closes and then retains the secondary member 518. This particular assembly is advantageous in that no tools are required for assembly or disassembly.

The mechanical fixations shown in FIGS. 14, 15, 16 and 17 all provide a means for readily disassembling the secondary member from the associated housing. In each case, it is relatively easy to remove the secondary member so that a replacement secondary member can be installed. In each case, the secondary member is a relatively simple piece and is used principally to provide the reflective surface. As the reflective surface degrades from use, a replacement secondary member with a freshly polished reflective surface can be installed on the dental mirror assembly without need for replacing any of the other components. Thus, in all these embodiments, there is provided a dental mirror in which the reflective surface is provided on a component which can be readily assembled to or removed from the remainder of the dental mirror assembly. This permits convenient and relatively inexpensive replacement of the reflective surface without the need to replace on anywhere near as frequent basis, the remainder of the parts contained within the housing and the handle.

Various amendments and substitutions can be made of the structures disclosed herein in the embodiments discussed in detail herein.

In the embodiments disclosed herein, it has been suggested that two different light sources be used for lighting the work zone of the mirror. As an alternative, the mirror assembly may be provided with only one light source moveable from a first position to a second position. In this case, it is desirable that there be means to manipulate the light field provided by that light source. This effectively provides two or more different light fields but from a single source. This may be accomplished by providing a light source and having the light source mounted in the handle portion for relative rotation thereto. When the dentist prefers a different light field from that currently in place, he rotates the light source relative to the handle, about the axis of the handle so the light field moves as desired. In a further alternative, the light source may be covered by a lens. Rather than rotating or moving the light source itself, means may be included to vary the directional output from the lens. Alternatively, this can be achieved by having a sleeve which is rotated so that only a portion of lens emits light while the remainder of the lens is opaque.

Preferably the handle portion is substantially tubular in nature. Any of the electronic components including compartments for holding batteries and the like, may be created in a separate insertable pieces. The separate insertable pieces may be removed from the handle portion to permit autoclaving for the appropriate parts while not requiring that all internal operating systems contained within the handle portion are subjected to the autoclaving temperatures.

Various other modifications may be made within the scope of the invention. The foregoing disclosure is to be considered illustrative only. The scope of the invention is defined in the appended claims.

What is claimed is:

1. A mirror assembly comprising
a handle portion and a head portion
the head portion including
a housing,
a rotor assembly, including a rotor,
rotor drive means,
a secondary member having a reflective surface,
attachment means for removably attaching the secondary member with respect to the rotor assembly for rotation therewith and,
bearing means for supporting the rotor relative to the housing for relative rotation of the rotor with respect to the housing, and wherein the attachment means comprises at least one magnet component and at least one magnetic component.

2. The mirror assembly of claim 1 wherein the magnet component is located on the housing.

3. The mirror assembly of claim 2 wherein the magnet component is an electro magnetic.

4. The mirror assembly of claim 1 wherein the bearing means includes at least one ball bearing.

5. The mirror assembly of claim 4 wherein the rotor has an axle, the axle having an axis.

6. The mirror assembly of claim 5 wherein the bearing means includes at least two ball bearings.

7. The mirror assembly of claim 6 wherein the bearing means includes at least one spring washer and the at least one spring washer is located between the at least two ball bearings to urge the at least two ball bearings axially away from one another.

8. The mirror assembly of claim 1 wherein the rotor drive means is an electric motor, and the motor comprises a stator and a rotating drive magnet.

9. The mirror assembly of claim 8 wherein the motor is a brushless motor.

10. The mirror assembly of claim 1 wherein the rotor drive means is a fluid driven turbine.

11. The mirror assembly of claim 1 further comprising at least one light source for lighting the work zone of the mirror and the work zone extends from 0.5 to 5 cm from the reflective surface.

12. The mirror assembly of claim 11 wherein the at least one light source is moveable between a first position relative to the head portion and a second position relative to the head portion each of the first and second positions defining a light field on either side of a lighting axis and the lighting axes are at an angle to one another.

13. The mirror assembly of claim 1 comprising at least two independent light sources, each light source having a light field on either side of a lighting axis, and the lighting axes are at an angle to one another.

14. The mirror assembly of claim 13 wherein the angle between the lighting axes is at least 45°.

15. The mirror assembly of claims 14 wherein the angle between the lighting axes is at least 90°.

16. The mirror assembly of claim 14 further comprising switch means for selecting functioning of the independent light sources one at a time.

17. The mirror assembly of claim 16 wherein the light sources are LED's.

18. The mirror assembly of claim 17 further comprising cooling means located within the handle portion for cooling the LED's.

19. The mirror assembly of claim 17 further comprising cooling means located within the handle portion for cooling the LED's wherein the cooling means includes a heat pipe.

20. The mirror assembly of claim 1 wherein the housing includes a base portion and a cap portion.

21. The mirror assembly of claim 20 wherein the cap portion is hermetically sealed to the base portion to create a hermetically sealed chamber therebetween which communicates with the handle.

22. The mirror assembly of claim 20 wherein the secondary member includes a planar surface and a first cylindrical wall surface, depending from the planar surface, the cylindrical wall having a first diameter.

23. The mirror assembly of claim 20 wherein the housing includes a second cylindrical wall extending away from the base portion, the second cylindrical wall having a second diameter.

24. The mirror assembly of claim 23 wherein the first diameter is smaller than the second diameter so that the first cylindrical wall is nested within the second cylindrical wall.

25. The mirror assembly of claim 24 wherein the planar surface of the secondary member is the reflective surface.

26. A secondary member for use with a dental mirror assembly said dental mirror assembly having a rotor assembly wherein said secondary member includes a reflective surface, said secondary member including attachment means for removeably attaching the secondary member with respect to the rotor assembly, and wherein the attachment means is a mechanical component, and wherein the mechanical component includes a shaft.

27. A mirror assembly comprising a handle portion and a head portion the head portion comprising a reflective surface, wherein the handle portion comprises at least one light source for lighting the work zone of the mirror and the work zone extends from 0.5 to 5 cm from the reflective surface,
and wherein the at least one light source is moveable between a first position relative to the head portion and a second position relative to the head portion each of the first and second positions defining a light field on either side of a lighting axis and the lighting axes are at an angle to one another.

28. The mirror assembly of claim 27 comprising at least two independent light sources, each light source having a light field on either side of a lighting axis, and the lighting axes are at an angle to one another.

29. The mirror assembly of claim 28 wherein the angle between the lighting axes is at least 45°.

30. The mirror assembly of claim 29 wherein the angle between the lighting axes is at least 90°.

31. The mirror assembly of claim 30 further comprising switch means for selecting functioning of the independent light sources one at a time.

32. The mirror assembly of claim 31 wherein the light sources are LED's.

33. The mirror assembly of claim 32 further comprising cooling means located within the handle portion for cooling the LED's.

34. The mirror assembly of claim 32 further comprising cooling means located within the handle portion for cooling the LED's wherein the cooling means includes a heat pipe.

35. A mirror assembly comprising
a handle portion and a head portion
the head portion including
a housing,
a rotor assembly, including a rotor, rotor drive means, a secondary member having a reflective surface, attachment means for removably attaching the secondary member with respect to the rotor assembly for rotation therewith and, bearing means for supporting the rotor relative to the housing for relative rotation of the rotor with respect to the housing wherein the rotor has an axle, the axle having an axis and wherein the bearing means includes at least two ball bearings and wherein the bearing means includes at least one spring washer and the at least one spring washer is located between the at least two ball bearings to urge the at least two ball bearings axially away from one another.

36. A secondary member for use with a dental mirror assembly said dental mirror assembly having a rotor assembly wherein said secondary member includes a reflective surface, said secondary member including attachment means for removably attaching the secondary member with respect to the rotor assembly and wherein the attachment means includes at least one magnetic component.

37. The mirror assembly of claim 35 wherein the attachment means comprises at least one magnet component and at least one magnetic component.

38. The mirror assembly of claim 37 wherein the magnet component is located on the housing.

39. The mirror assembly of claim 38 wherein the magnet component is an electro magnetic.

40. The mirror assembly of claim 35 wherein the housing includes a base portion and a cap portion.

41. The mirror assembly of claim 40 wherein the cap portion is hermetically sealed to the base portion to create a hermetically sealed chamber therebetween which communicates with the handle.

42. The mirror assembly of claim 40 wherein the secondary member includes a planar surface and a first cylindrical wall surface, depending from the planar surface, the cylindrical wall having a first diameter.

43. The mirror assembly of claim 40 wherein the housing includes a second cylindrical wall extending away from the base portion, the second cylindrical wall having a second diameter.

44. The mirror assembly of claim 43 wherein the first diameter is smaller than the second diameter so that the first cylindrical wall is nested within the second cylindrical wall.

45. The mirror assembly of claim 44 wherein the planar surface of the secondary member is the reflective surface.

46. A mirror assembly comprising a handle portion and a head portion the head portion including a housing, a rotor assembly, including a rotor, rotor drive means, a secondary member having a reflective surface, attachment means for removably attaching the secondary member with respect to the rotor assembly for rotation therewith and, bearing means for supporting the rotor relative to the housing for relative rotation of the rotor with respect to the housing, the attachment means includes a mechanical component located on the secondary member and a corresponding mechanical component located on the rotor assembly, and the mechanical component located on the secondary member includes a shaft and the corresponding mechanical component located on the rotor assembly includes a shaft having a bore, and said bore is adapted to receive said shaft located on said secondary member, and wherein said bore includes chuck means and wherein said shaft attached to said secondary member includes an end portion adapted for fitting into said chuck means.

47. The mirror assembly of claim 46 wherein said housing includes a lower shell and wherein said lower shell includes a flexible portion, said flexible portion having an upwardly projecting finger adapted to cause movement of said chuck from a closed position to an open position.

* * * * *